United States Patent [19]

Tzakis

[11] Patent Number: 5,188,638
[45] Date of Patent: Feb. 23, 1993

[54] APPARATUS AND METHOD FOR PREFORMING ANASTOMOSIS FASTENER SECUREMENT OF HOLLOW ORGANS

[76] Inventor: Andreas G. Tzakis, 505 Amberson Ave., Pittsburgh, Pa. 15232

[21] Appl. No.: 831,937

[22] Filed: Feb. 6, 1992

[51] Int. Cl.$^5$ ............................................. A61B 17/00
[52] U.S. Cl. .................................. 606/153; 606/151; 227/175; 227/176; 227/178
[58] Field of Search ................... 606/151, 153; 227/19, 227/175, 176, 181, 178, 179

[56] References Cited

U.S. PATENT DOCUMENTS

| | | | |
|---|---|---|---|
| 3,519,187 | 7/1970 | Kapitanov et al. | 227/19 |
| 3,973,570 | 8/1976 | Razgulov et al. | 606/153 |
| 4,047,654 | 9/1977 | Alvarado | 227/19 |
| 4,310,115 | 1/1982 | Inoue | 227/19 |
| 4,681,108 | 7/1987 | Rosati et al. | 606/155 |
| 4,703,887 | 11/1987 | Clanton et al. | 227/19 |
| 4,917,090 | 4/1990 | Berggren et al. | 606/153 |
| 4,929,240 | 5/1990 | Kirsch et al. | 606/151 |

FOREIGN PATENT DOCUMENTS

| | | |
|---|---|---|
| 0137685 | 4/1985 | European Pat. Off. . |
| 0659146 | 4/1979 | U.S.S.R. . |
| 0995765 | 7/1981 | U.S.S.R. . |
| 1237183 | 6/1986 | U.S.S.R. ............... 227/178 |
| 2038692 | 7/1980 | United Kingdom . |
| 2108418 | 5/1983 | United Kingdom . |

OTHER PUBLICATIONS

Steichen, F. M., et al., History of Mechanical Devices and Instruments for Suturing, 1982, Yearbook Medical Publishers, pp. 2-52.

Tzakis, A. G. et al., A Simple and Safe Roll Over Sleeve Technique for Venous Anastomosis, Jan. 1990, Surgery, Gynecology & Obstetrics, vol. 170, p. 77.

Primary Examiner—Stephen C. Pellegrino
Assistant Examiner—Jeffrey A. Schmidt
Attorney, Agent, or Firm—Carothers & Carothers

[57] ABSTRACT

An anastomosis fastening technique wherein an annular fastener securing anvil is positioned over the end portion of a first hollow body organ to be joined to a second hollow body organ end or side portion and this first organ end is everted outwardly back over the anvil thereby forming a cuff. The anvil is provided with prepositioned and annularly disposed fastener securing devices on the exterior surface. The second hollow body organ and/or side portion is then positioned over the cuff of the first hollow body organ such that the intimal portions thereof to be anastomosed are in intimal coaptation. An anastomotic surgical fastener driving instrument with fastener cartridges therein, and which conforms in shape to the outer annular contours of the anvil is coaxially applied over the anvil with the organ portions positioned therebetween and the fastener driving instrument is then actuated to fasten the coaptating organ portions together. The organ portions to be anastomosed may first be tied down to the anvil. The fastener driving instrument is also keyed to the anvil for proper positioning of the fasteners relative to the anvil fastener securing devices prior to actuating the fastener driving instrument. The fasteners may be in the form of surgical staples, nails or tacks.

23 Claims, 5 Drawing Sheets

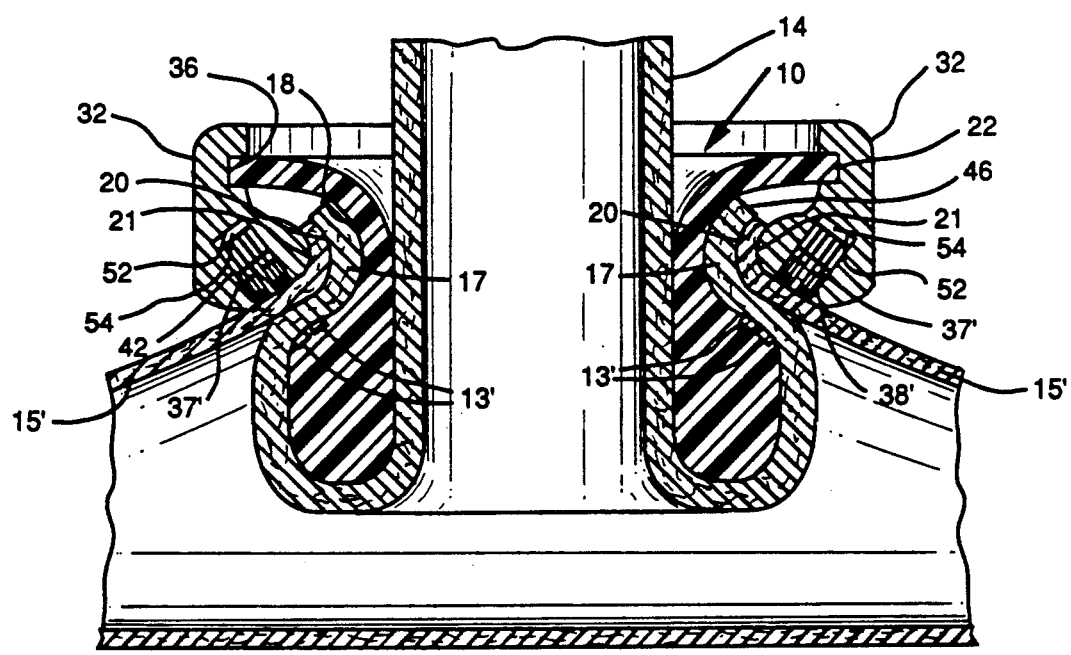
FIG. 8
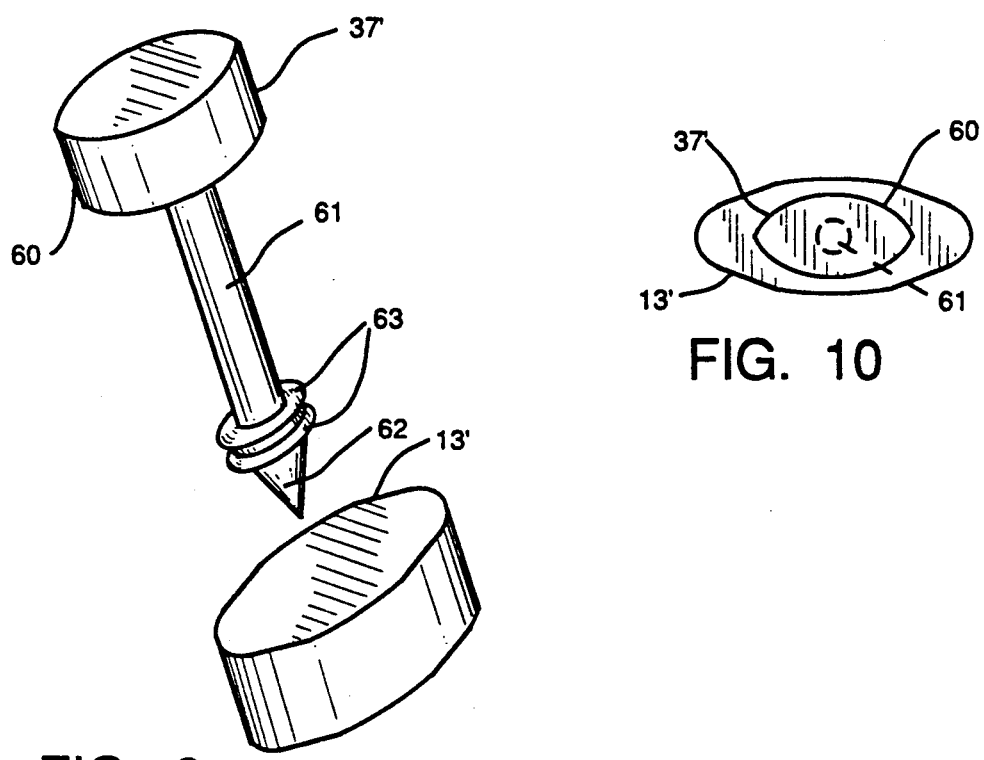
FIG. 9
FIG. 10

APPARATUS AND METHOD FOR PREFORMING ANASTOMOSIS FASTENER SECUREMENT OF HOLLOW ORGANS

The present invention pertains to the field of medicine and more particularly to surgery. More specifically, the present invention generally relates to surgical suturing devices and methods for applying an anastomosis onto hollow organs, e.g. the organs of the digestive tract or blood vessels, for instance, for joining them together in end-to-end or end-to-side utilizing fastener securing techniques.

In various surgical procedures, speed of performing the operation can become extremely critical. For example, in transplant surgery, it is very important to reconnect the supply of blood to the transplanted organ as soon as possible in order to minimize damage to the organ. Such blood vessels are now normally anastomosed end-to-end or end-to-side by suturing techniques. One such suturing technique is described in the article entitled A Simple and Safe Roll Over Sleeve Technique for Venous Anastomosis, by the present inventor in conjunction with Andrei C. Stieber SURGERY, Gynecology & Obstetrics, January, 1990, Vol. 170 at page 77.

Such suture anastomosis procedures generally take the skilled surgeon anywhere from ten to twenty minutes to complete for each anastomosis and for many organs a number of such connections are required.

Presently, there are no known simple, yet foolproof, anastomosis stapling or other fastener securing techniques for the vascular system. The blood vessels being much smaller than other hollow body organs, such as the intestines, present a difficult problem for conventional stapling techniques. Additionally, with the blood vessels, any stapling anastomosis must be accomplished completely from the exterior of the blood vessels being joined as there is obviously no way to remove parts from within the blood vessel after the anastomosis is performed.

A major obstacle in the creation of a surgical stapling or other fastener securing instrument for performing vascular anastomosis is the present day inability of such devices to automatically secure intimal coaptation of the two vessels to be anastomosed. It is a principal object of the present invention to eliminate this obstacle and to provide an apparatus and method which permits and provides easy and quick vascular anastomosis using the aforedescribed rollover sleeve or cuff technique with surgical fastener securement. The same techniques may, of course, also be applied to other anastomosis procedures such as on the GI tract.

It is a principal object of the present invention to provide an apparatus and method for performing anastomosis stapling or other fastener securement of hollow organs which provides a leak proof connection of adequate tensile strength and avoids trauma to the vessel or organ and promotes rapid and thorough healing. It is a further object of the present invention to provide such an apparatus and method which will permit anastomosis of hollow body organs by a surgeon with minimum skill requirement in a matter of seconds as opposed to minutes.

The apparatus and method of the present invention provide an annular, but not necessarily circular, and preferrably ellipsoid shaped, fastener securing anvil adapted in size and shape to annularly encompass the outer periphery of a first hollow organ adjacent the severed end thereof to be anastomosed to a severed end or side of a second hollow organ. This annular anvil is provided with a plurality of prepositioned and annularly disposed fastener securement devices on its exterior.

This annular fastener securement anvil is selected to have an inner circumference which is compatable with the outer circumference of the hollow body organ to which it is to be applied. The annular anvil is then slid over an open end portion of the first hollow body organ and the open end portion of that first hollow body organ is rolled outwardly back or everted outwardly and back over the annular anvil thereby forming a cuff on the end of the first hollow body organ over top of a portion of the anvil. The hollow body organ end cuff overlies the fastener securement devices on the exterior of the anvil.

Then a second open hollow body organ end or side portion to be anastomosed to the first hollow body organ end portion is positioned or slid over the aforedescribed cuff portion of the first hollow body organ end such that the intimal portions of the organs to be anastomosed are in intimal coaptation.

The cuff end of the first hollow body organ is preferably tied down with a simple suture to the fastener securing anvil, and in a similar fashion the second hollow body organ end or side portion is also preferably tied down to the anvil over its overlying hollow body organ cuff end with another simple suture. This initially maintains the intimal ends thereof in coaptation.

Thereafter an anastomotic surgical fastener driving instrument which has fastener cartridges therein containing a plurality of fasteners, and also has an internal configuration which conforms annularly in shape to the outer annular contours of the fastener securing anvil with the coaptating organ ends to be anastomosed, is positioned thereover. The fastener driving instrument is thus annularly or coaxially clamped over the anvil with its overlying coaptating organ portions positioned thereon and the fastener driving instrument is also keyed to the anvil for proper positioning of the fasteners relative to the anvil fastener securing devices. After so securing the surgical fastener driving instrument, it is actuated thereby driving the fasteners and fastening the coaptating organ portions together utilizing the fastener securing devices or means on the anvil to secure the fasteners.

The annular anvil is preferably formed in split halves which are either lightly glued or otherwise connected together so that it is provided as a unitary annular device which may be easily slid over the outside of the organ end in coaxial fashion without falling apart. After the fastener securing anastomosis procedure has been performed, the surgical fastener driving instrument may be unclamped or otherwise removed and the anvil may be severed or split in half at its half junctures for easy removal.

The fasteners may be provided in different size to properly suit the particular anastomosis situation and the fasteners will generally be applied annularly in indian file fashion, and they also may be further applied in double staggered annular rows.

The fasteners may be of various types, such as, conventional U-shaped surgical staples or in the form of a surgical nail or tack. Nails or tacks are preferable for use with arteries having arterioscloratic plaque as the artery walls are too hard for proper or easy securement with conventional surgical staples. Surgical staples are more acceptable for use on veins and the GI tract which are softer and more pliable.

Generally, the outer annular contour of the anvil will be made ellipsoid so that it can be utilized near clamped ends of vessels, which by virtue of having been clamped near the cut end will present an ellipsoid shape. However, in situations such as in intestinal anastomosis or microvascular anastomosis, the fastener securing anvil can be formed in circular fashion. The surgical fastener driving instrument will of course have to conform respectively to the different anvil configurations.

Other objects and advantages appear in the following description and claims.

The accompanying drawings show, for the purpose of exemplification without limiting the invention or claims thereto, certain practical embodiments illustrating the principals of this invention wherein:

FIG. 1 is a perspective view in front elevation showing one embodiment of the fastener securing anvil portion of the anastomosis apparatus of the present invention;

FIG. 2 is a perspective view in front elevation showing the anvil structure of FIG. 1 with a first hollow organ end everted thereover to form a cuff shown in vertical mid cross section as seen along section line II—II of FIG. 1, and further illustrating in exploded fashion the open end of a second hollow body organ to be positioned or slid over top of the anvil with its overlying first hollow body organ end cuff;

Figure 3:
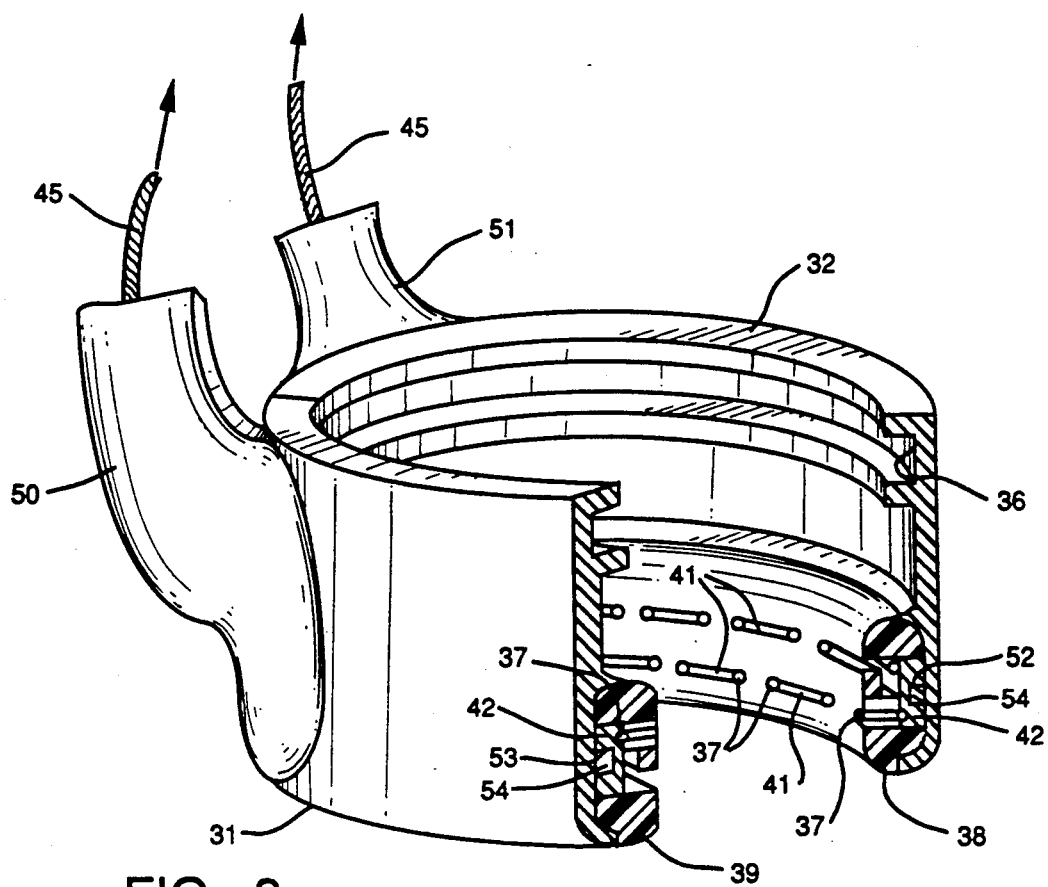
FIG. 3 is a perspective view in front elevation of the jaws containing fastener containing cartridges therein of an anastomotic surgical fastener driving instrument, which jaws are to be positioned over the fastener securing anvil shown in FIG. 1 with the hollow body organ ends to be anastomosed positioned or confined therebetween as illustrated next in FIG. 4.
Figure 4:
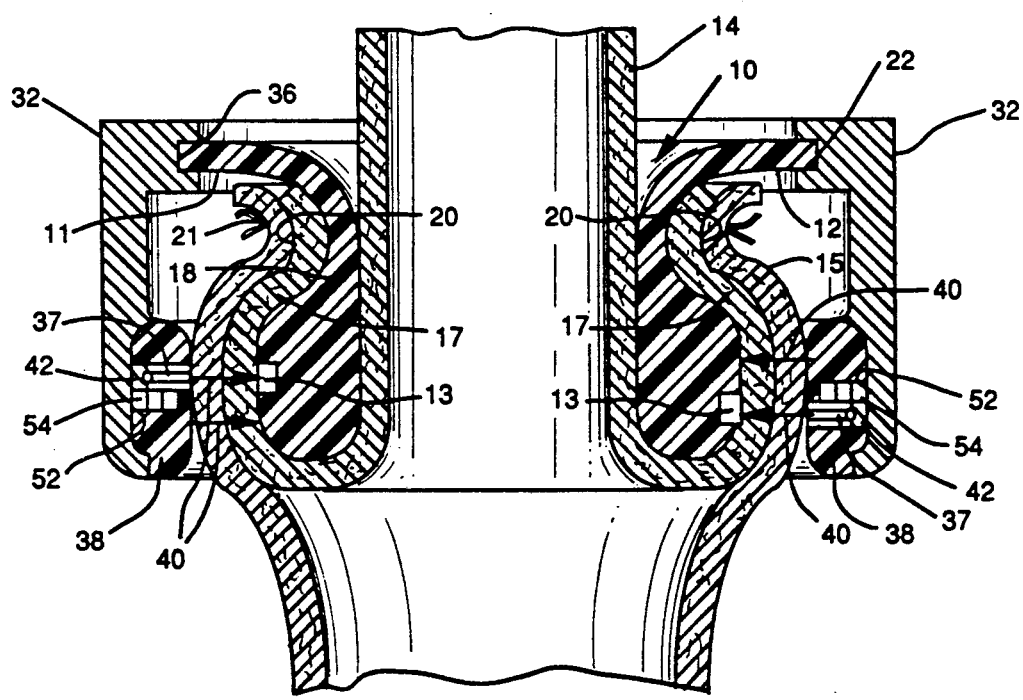
FIG. 4 is a front view in vertical mid cross section illustrating the anastomotic surgical fastener driving instrument jaws of FIG. 3 positioned over the fastener securing anvil of FIG. 1 with the hollow body organ ends to be anastomosed positioned therebetween in intimal coaptation.
Figure 5:
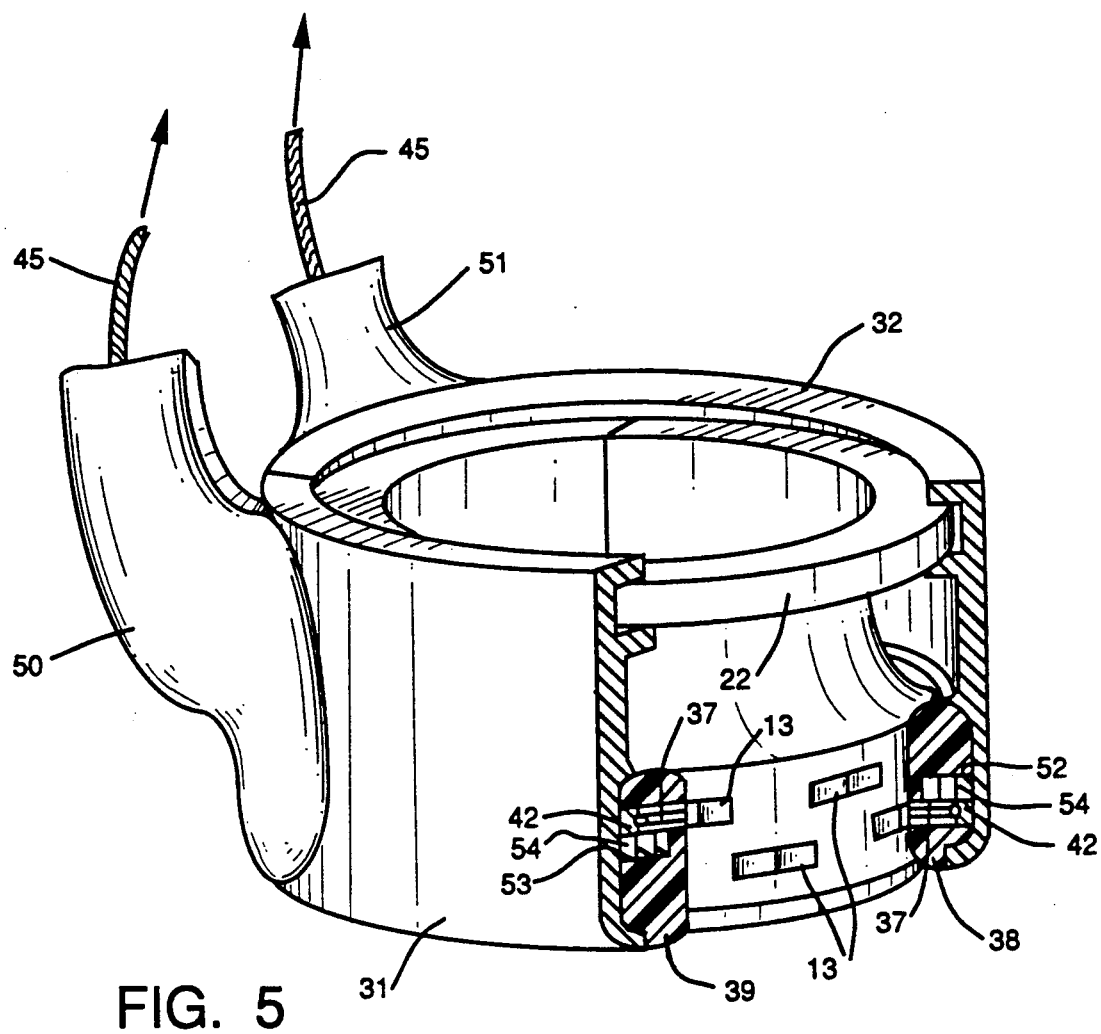
Figure 6:
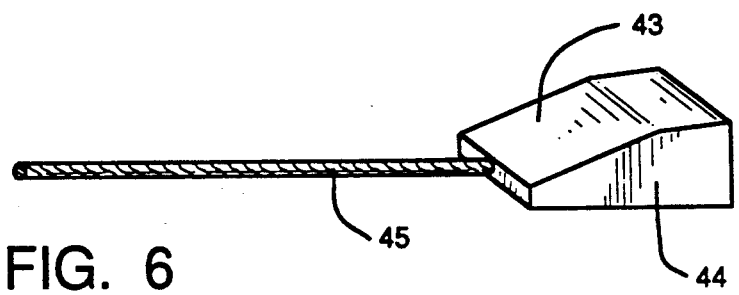
Figure 7:
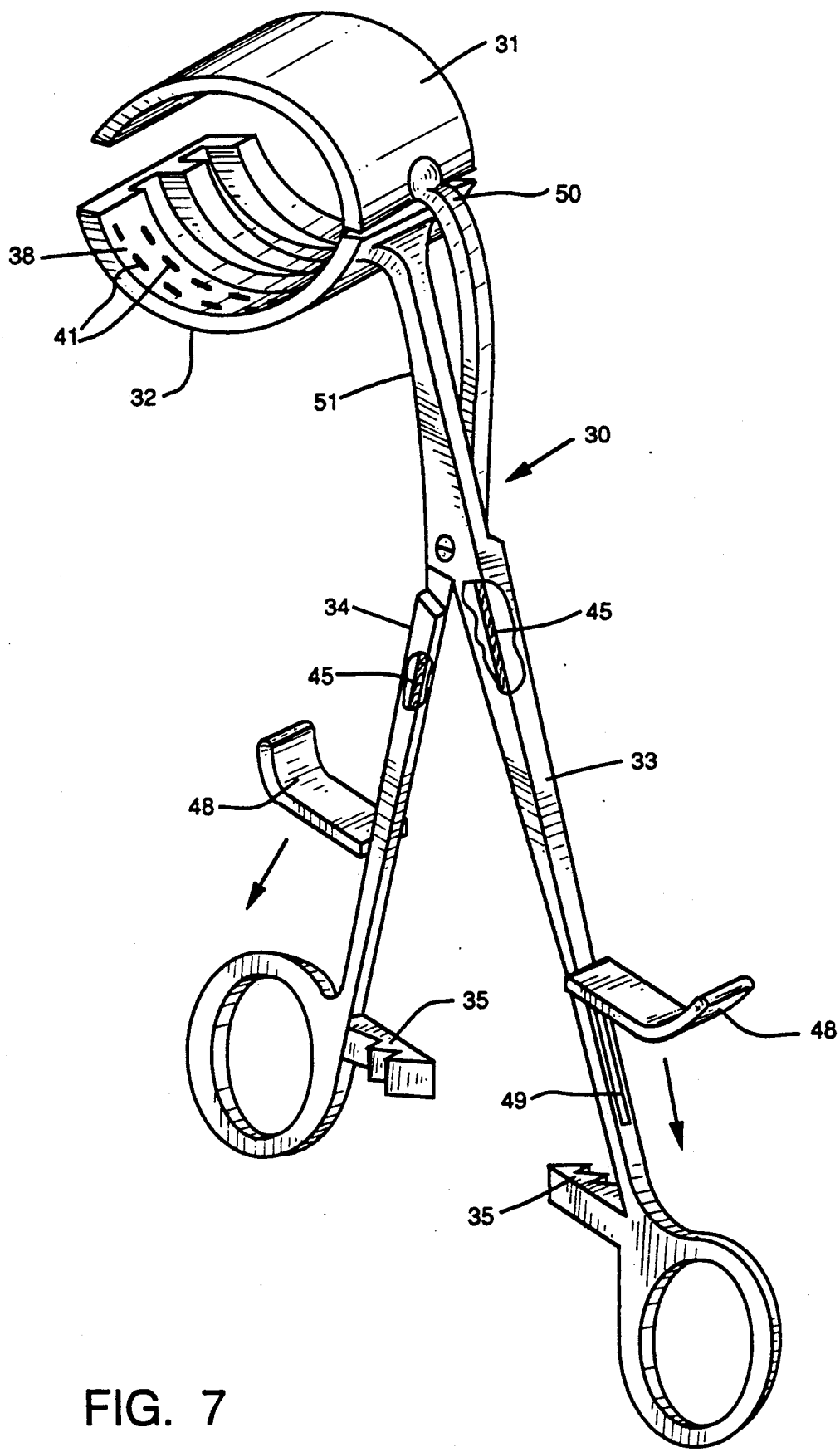

FIG. 5 is a perspective view in front elevation of the combined apparatus illustrated in FIG. 4 with the hollow organ ends removed and with the jaws of the anastomotic surgical fastener driving instrument shown in partial vertical section to permit clearer internal viewing of the two parts keyed together such that the fasteners contained within the jaws are prepositioned over the fastener securing devices or means on the anvil;

FIG. 6 is a perspective view in side elevation of the distal end of one of the actuating lines with its actuating ramp head of the anastomotic surgical fastener driving instrument which is utilized for driving fasteners from within one of the fastener cartridges found within the jaws of the fastener driving instrument shown in FIGS. 3, 4, 5 and 7;

FIG. 7 is a perspective view showing the entire anastomotic surgical fastener driving instrument, including the jaws thereof illustrated in FIGS. 3, 4 and 5.

FIG. 8 is a front view in vertical mid cross section illustrating a variation in the anastomotic surgical fastener driving instrument jaws and the cooperating fastener securing anvil of FIG. 4 as adapted for end-to-side anastomosis and also utilizing a different fastener;

FIG. 9 is a perspective view of the fastener utilized in the structure shown in FIG. 8; and FIG. 10 is a top or plan view of the fastener shown in FIG. 9.

Figure 1:
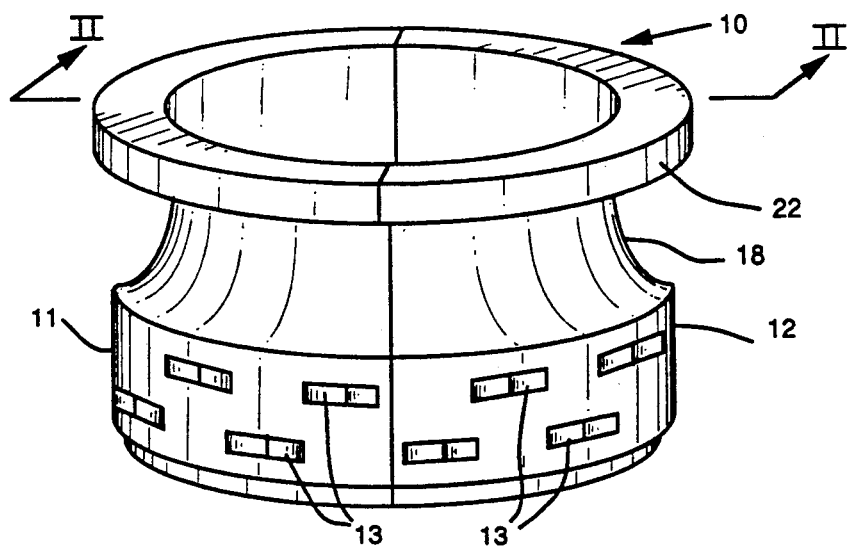
Figure 2:
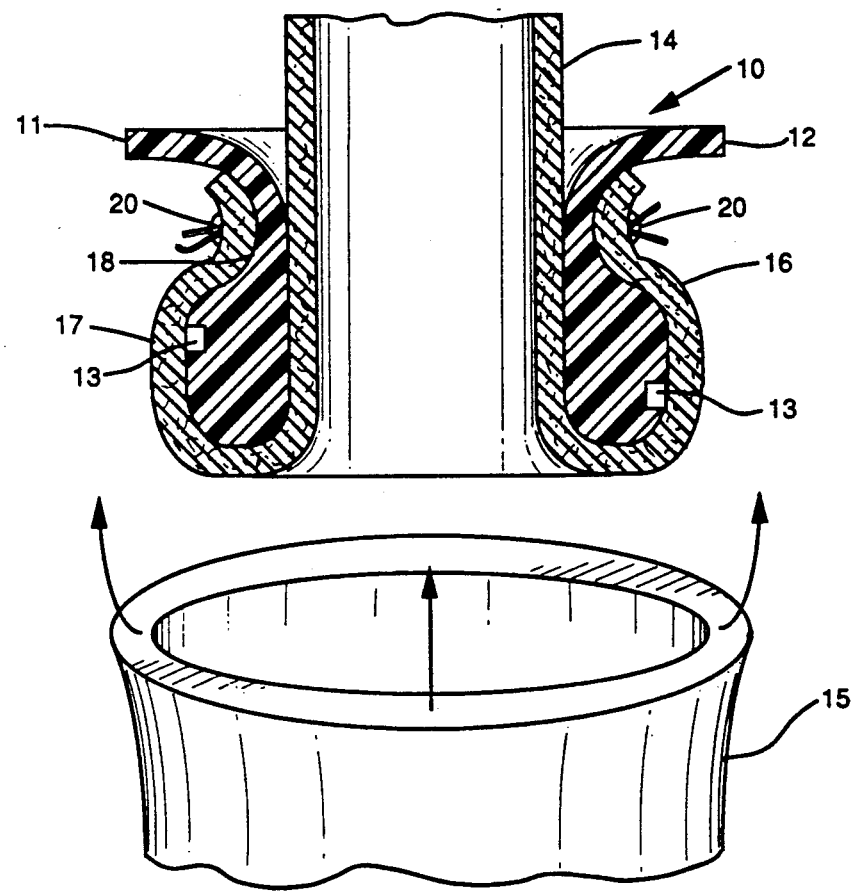

Referring to FIGS. 1 and 2, an annular fastener securing anvil portion 10 of the apparatus of the present invention is shown. In FIG. 1 it is illustrated in an ellipsoid configuration for the reasons previously explained and it is further provided in split halves 11 and 12 which are lightly glued together so that they may be severed into their respective split halves after the anastomosis procedure is accomplished.

Anvil 10 is provided with prepositioned and annularly disposed fastener securing means in the form of staple-clinching grooves 13 on the exterior thereof which are alligned in indian file fashion in double staggered annular rows.

Reference is next made in particular to FIG. 2 to illustrate the first step of the anastomosis procedure of the present invention wherein the first hollow body organ 14 to be joined to a second hollow body organ 15, both here illustrated in the form of blood vessels, has its open end portion 16 positioned coaxially through the anvil 10 and then everted outwardly back over anvil 10 forming the cuff end 17 which overlies the outer annular surface of anvil 10.

Anvil 10 is additionally provided with annular suture groove 18 so that the cuff end 17 of vessel 14 can be annularly tied down to anvil 10 in annular groove 18 with suture 20. This can be, for example, a simple single looped tie or it can be a purse string suture or the like.

Then the second hollow organ end portion 15 is slid over the cuff portion 17 of the first hollow body organ as suggested or indicated by the arrows in FIG. 2 so that the inside end portions or intimal portions of these organs to be anastomosed are in intimal coaptation as illustrated best in FIG. 4. The second hollow body organ end 15 is also tied down the anvil 10 in the groove area 18 with suture 21.

Next, the jaws 31 and 32, shown independently in FIG. 3, of the anastomotic surgical fastener driving instrument 30 shown in FIG. 7, are coaxially positioned over anvil 10 with the end portions 17 and 15 of the respective hollow body organs positioned therebetween as best illustrated in FIG. 4.

For a clearer view of the interior portions, this is also illustrated in FIG. 5 with the hollow organ ends 17 and 15 removed.

The anastomotic surgical fastener driving instrument shown in FIG. 7 is in the form of a staple driving instrument and generally takes on the configuration of a hemostat with conventional handles 33 and 34 and the conventional slip ratchet device 35 for maintaining handles 33 and 34 together when they are squeezed toward each other to bring jaw halves 31 and 32 together in clamping engagement coaxially over anvil 10 with the organ ends 15 and 17 positioned in intimal coaptation therebetween for anastomosis stapling as best illustrated in FIG. 4.

The interior annular combined contours of the jaws 31 and 32 when clamped together form an annular ellipsoid configuration conforming to the outer annular contours of anvil 10 for uniformly clamping the cuff portion 17, from the first hollow organ end 14 which is everted over the anvil, in intimal coaptation with the end portion 15 of the second hollow body organ positioned over the cuff.

A guide means is also provided jaws 31 and 32 and anvil 10 in the form of an outwardly extending keying lip 22 which annularly extends over at least a portion of anvil 10, and a conforming and cooperating annular keying groove 36 in the interior of jaws 31 and 32 of instrument 30 when clamped together to annularly receive lip 22.

It should be realized and understood that annular lip 22 on anvil 10 need not be continuous as shown and may be segmented. For example, annular lip 12 may, if desired, extend only for short portions on opposite sides of anvil 10 to permit easier access to groove 18 with the surgeons fingers in order to permit easier tying of the sutures 20 and 21.

This keying arrangement makes certain that jaws 31 and 32 are clamped in predetermined allignment with the anvil 10 so that the respective individual staples 37, prealligned within the respective staple cartridges 38 and 39 of jaws 32 and 31 respectively, are properly prepositioned on the inside of jaws 31 and 32 for cooperation with the fastener securing means in the form of staple-clinching grooves 13 on anvil 10 for clinching said staples when driven inwardly towards the anvil 10 as indicated or illustrated by the arrows 40 shown in FIG. 4.

The conventional surgical U-shaped staples 37 are respectively received in their guide slots 41 for proper prepositioning and the staples 37 are driven inward through intimal coaptating hollow organ end portions 15 and 17 for clinching in grooves 13 on anvil 10 by driving slides 42. Driving slides 42 force the staples 37 annularly inward when they are respectively driven by the ramp surface 43 (see FIG. 6) on the head 44 of the fastener or staple drive draw lines 45.

Two of these draw lines 45 are provided as may be seen in FIG. 7.

The proximal ends of these two lines 45 are connected inside hollow arms 33 and 34 to the inside ends (not shown) of staple actuating levers 48 of instrument 30.

When the hemostat arms 33 and 34 are engaged and clamped together or held together by device 35, the operator may then pull both handle ends 48 downwardly or outwardly as indicated by the arrows with one's fingers simultaneously or independently which causes levers 48 to guideably slide in slots 49 and accordingly forces or draws lines 45 outwardly as depicted by the arrows in FIGS. 3 and 5.

Lines 45 are constructed of very strong flexible thread or line material, such as metal or plastic, and they extend upward on into the hollow interior of the forearms 50 and 51 of instrument 30 and on through slots 52 and 53 respectively of fastener or staple cartridges 38 and 39, such that their respective heads 44 are drawn or pulled through slots 52 and 53 when levers 48 are slidably actuated.

Heads 44 are each respectively positioned so that the respective ramp surfaces 43 thereof face inward and when the heads 44 are drawn through their slots, these ramp heads 43, respectively and sequentially, engage the ramped slide surfaces 54 and 55 of the quided staple driving slides 42 thereby forcing them radially inward to drive the staples as previously described in a sequential operation.

In view of the fact that there is some curvature of the respective staple cartridges 38 and 39, the flexibility of lines 45 permits heads 44 to continue on through their respective slots 52 and 53 without binding.

The anastomotic surgical staple driving instrument 30 may be constructed of metal or it may also be constructed of a rugged plastic and it may be designed for a single use so that it is packaged in a sterilized condition and then disposed of following a single use or it can be reused by inserting new staple cartridges 38 and 39.

The staple driving slides 42 may also be constructed of plastic as may the general body structure of the staple cartridges 38 and 39.

The general configuration of staple cartridges 38 and 39 and the general configuration of the draw line head 44 as seen in FIG. 6 is not new and this type of stapling mechanism may be readily seen on the market as manufactured by a number of different companies. For example, this specific type of staple actuating structure may be seen in the PROXIMATE (trademark) cutter and anastomatic surgical stapling instrument manufactured by Johnson and Johnson as model number PLC50.

Anvil 10 is also preferably constructed of or molded of rigid plastic.

Referring next to FIG. 8, a variation of the method and apparatus of the present invention in illustrated for utilizing the principals of the present invention for end-to-side anastomosis of blood vessels, as opposed to the end-to-end anatomosis illustrated in the previous figures.

While the design configurations of the structure shown in FIG. 8 vary somewhat from the structure previously illustrated, nevertheless, the overall design and function is similar and accordingly identical parts are numbered with identical reference numerals and similar parts are referenced with the same reference numerals with a prime indication added.

Instead of anastomosing the cuff portion 17 of blood vessel 14 to an end 15 of another blood vessel as previously illustrated, here the cuff portion 17 is being anastomosed to a side portion of blood vessel 15'. The side opening edge portion 46 in blood vessel 15' is created by cutting a longitudinal slit in the side of blood vessel 15'.

The fastener securing anvil 10 with its overapplied blood vessel cuff end portion 17 is inserted downwardly into this opening 46 and then pulled back upward so that the side opening porition 46 overlies and is in intimal coaptation with cuff 17 as shown in the figure and the side portion 46 is then also tied down with suture 21 to the annular groove portion 18 of anvil 10.

In this embodiment, the fasteners utilized to anastomose the blood vessels are not surgical staples, but are instead surgical nails or tacks 37'. Staples may not be suitable in all situations for fasteners where the organs being joined are extremely hard, such as is encountered with arteries having arteriosclorotic plaque. In this situation, these surgical staples or nails 37 are preferable as they can more easily penetrate the hard artery walls.

These surgical nails or tacks are illustrated in an enlarged fashion in FIGS. 9 and 10.

The staple clinching grooves 13 of the prior illustrated structures is replaced with fastener securing means or devices in the form of nai end securing caps 13'.

Each of the surgical nails 37' is primarily constructed of a nail head 60 which is provided with a nail shaft 61 having at its distal end a sharp point 62 for driving the nail shaft 61 downwardly into the fastener securing device or cap 13' which is in the form of a pad.

Nail head 60 is constructed of a rigid plastic or metal and its connected nail shaft 61 is either also constructed of a quality rigid plastic or of a metal, such as, surgical stainless steel which will not be rejected by ones immune system.

Securing cap or pad 13' is also constructed of a rigid plastic, but of a plastic which is not so brittle that it cannot be penetrated by the point 62 of fastener 37' when driven down therein to penetrate the cap 13'.

Nail fasteners 37' are driven inwardly in the same fashion as the staples 13 were driven in the previous embodiment through the use of guided fastener driving slides 42.

Once the fasteners 37' have been driven inwardly to penetrate the side opening portion 46 and the cuff end portion 17, the points 62 thereof will also be driven into the underlying nail caps 13' positioned and retained in anvil 10, and shaft 61 of the nail fasteners 37' will be driven sufficiently far into the underlying nail securing caps 13' so that the annular securing ribs 63 on the bottom of shaft 61 will also penetrate into the securing cap 13'.

Annular ribs 63 are conventional nail fastening ribs which are sloped on their forward edges to permit easy penetration into the caps 13' but are not sloped on their upper sides so that they will grip within the caps 13' and the fastener 37' cannot be removed or dislodged from cap 13'.

The material selected for the nail securing caps 13' is selected as a plastic which will most suitably grip the nail end together with its ribs 63 in penetration. For this purpose a plastic which is not brittle, such as, TEFLON (Trademark) is preferable.

The fastener heads 60 are also constructed in an oval fashion so that they may easily slide in and be guided within the corresponding guide slots 41 without rotating or tilting. In a similar fashion, the fastener securing caps 13' are also configured in an oval fashion so that they may be more readily retained within cooperating recesses annularly positioned about the outer contours of anvil 10.

I claim:

1. Apparatus for performing anastomosis on hollow organs comprising: an annular hollow sleeve shaped fastener securing anvil formed in size and shape to annularly encompass the outer periphery of a first hollow organ adjacent a severed end thereof to be anastomosed to a severed end or side of a second hollow organ, said anvil having a plurality of prepositioned and annularly disposed fastener securing means on the exterior thereof; an anastomotic surgical fastener driving instrument unattached to said anvil and having opposing clamp jaws, the interior annular combined contours of said jaws when clamped together form an annulus, and conform to outer annular contours of said anvil for annularly confining therebetween for anastomosis a cuff portion formed from a first hollow organ end everted over said anvil in intimal coaptation with an end or side portion of a second hollow organ positioned over the cuff formed on the first organ end; guide means on said anvil and jaw for keying said jaws, when clamped, in predetermined alignment with said anvil; fastener cartridge means retained in at least one of said jaws with fasteners prepositioned along the inside thereof for cooperation with said fastener securing means on said anvil for securing said fasteners when driven inwardly toward said anvil; and fastener driving means on said instrument for driving said fasteners inwardly through intimal coaptating hollow organ portions for securing by said fastener securing means on said anvil.

2. The apparatus of claim 1 wherein said annular anvil is formed in split halves.

3. The apparatus of claim 2 wherein said split halves are lightly glued or connected together for permitting intentional severing thereof.

4. The apparatus of claim 2 including an annular suture groove extending about an outer periphery of said anvil for providing a suture groove for tying an everted cuff end portion of a hollow organ annularly down to said anvil and for also tying a hollow organ end or side opening edge portion to the cuff end portion in intimal coaptation.

5. The apparatus of claim 4 wherein said fastener cartridge means are retained in all of said jaws.

6. The apparatus of claim 5 wherein said fastener driving instrument is provided with two of said jaws.

7. The apparatus of claim 6 wherein said fastener securing means are arranged about said anvil in indian file fashion.

8. The apparatus of claim 7 wherein said fastener securing means are provided in double staggered lines about said anvil.

9. The apparatus of claim 4 wherein said guide means is comprised of an outwardly extending keying lip annularly extending over at least a portion of said anvil and positioned on an end thereof opposite said fastener securing means with said suture groove positioned therebetween, and a conforming and cooperating annular keying groove in the interior of said jaws of said instrument, when clamped together, to receive said lip.

10. The apparatus of claim 1 wherein said annular anvil is ellipsoid in shape.

11. The apparatus of claim 1 wherein said fasteners are U-shaped staples and said fastener securing means are staple-clinching grooves for clinching said staples.

12. The apparatus of claim 1 wherein said fasteners are nails and said fastener securing means are nail-end securing caps for securing said nails when driven therein.

13. The apparatus of claim 12 wherein said nails have nail shaft tips provided with annular gripping ribs which grip said caps when said tips are driven therein.

14. The apparatus of claim 13 wherein said caps are solid pads constructed of plastic material which said nail tips may be driven into.

15. A method for joining hollow body organs by anastomosis fastener securement comprising the steps of: applying an annular fastener securing anvil over an open end portion of a first hollow body organ to be joined to a second open hollow body organ end or side portion and everting said first open end portion outwardly back over said anvil thereby forming a cuff portion, said anvil having a plurality of prepositioned and annularly disposed fastener securing means on the exterior thereof under the cuff portion; positioning said second open hollow body organ end or side portion over said cuff portion of said first hollow body organ such that the intimal portions of said organs to be anastomosed are in intimal coaptation; positioning an anastomotic surgical fastener driving instrument, which has at least one fastener cartridge therein containing a plurality of fasteners and conforms in shape to outer annular contours of said anvil, annularly over said anvil and said organ portions with said organ portions positioned on said anvil in intimal cooptation; and actuating said fastener driving instrument and thereby fastening and coaptating organ portions together by driving the fasteners therethrough and securing them with said fastener securing means.

16. The method of claim 15 wherein said annular anvil is formed in split halves which are lightly glued or connected together, and including the step of severing said anvil split halves after the step of actuating said fastener driving instrument.

17. The method of claim 16 including the step of respectively securing said intimal cooptating organ portions to be anastomosed to said anvil prior to actuating said fastener driving instrument.

18. The method of claim 17 wherein said anvil is provided with an annular suture groove extending about an outer periphery thereof, and said step of securing said cooptating organ portions is accomplished by annularly tying them down to said anvil in said annular groove with sutures, and removing said sutures immediately prior to the step of severing said anvil into halves.

19. The method of claim 18, wherein said instrument is provided with two fastener cartridges.

20. The method of claim 19 wherein the fasteners are annularly applied indian file.

21. The method of claim 20 wherein said fasteners are applied in double staggered annular rows.

22. The method of claim 15 including the step of keying said fastener driving instrument to said anvil for proper positioning of the fasteners relative to said anvil fastener securing means prior to the step of actuating said fastener driving instrument.

23. The method of claim 22 wherein said anvil is shaped as an ellipsoid.

* * * * *